United States Patent
Codignola

(10) Patent No.: US 6,833,472 B2
(45) Date of Patent: Dec. 21, 2004

(54) PROCESS FOR THE PURIFICATION OF AROMATIC CARBOXYLIC ACIDS

(75) Inventor: Franco Codignola, Milan (IT)

(73) Assignee: Eurotecnica Development and Licensing SpA (IT)

( * ) Notice: Subject to any disclaimer, the term of this patent is extended or adjusted under 35 U.S.C. 154(b) by 57 days.

(21) Appl. No.: 10/312,353

(22) PCT Filed: Jun. 13, 2001

(86) PCT No.: PCT/EP01/06751

§ 371 (c)(1),
(2), (4) Date: Jan. 9, 2003

(87) PCT Pub. No.: WO02/06200

PCT Pub. Date: Jan. 24, 2002

(65) Prior Publication Data

US 2003/0181755 A1 Sep. 25, 2003

(30) Foreign Application Priority Data

Jul. 14, 2000 (IT) ..................................... MI2000A1599

(51) Int. Cl.⁷ .............................................. C07C 51/42
(52) U.S. Cl. ..................................................... 562/485
(58) Field of Search ................................. 562/485, 494

(56) References Cited

U.S. PATENT DOCUMENTS 5,527,957 A   6/1996   Hindmarsh et al. .......... 562/414

FOREIGN PATENT DOCUMENTS

| DE | 1147571 | 4/1963 | |
| FR | 1355273 A | 6/1964 | |
| JP | 9-104653 | 7/1996 | ..................... 63/26 |
| JP | 9-151160 | 6/1997 | ..................... 63/26 |
| WO | WO 92/18454 | 10/1992 | ..................... 51/43 |
| WO | WO 93/24440 | 12/1993 | ..................... 63/26 |
| WO | WO 96/11899 | 4/1996 | ..................... 41/265 |
| WO | WO 97/30963 | 8/1997 | ..................... 63/26 |
| WO | WO 98/29378 | 7/1998 | .................. 51/265 |

*Primary Examiner*—Paul J. Killos
(74) *Attorney, Agent, or Firm*—Stephen M. Nipper; Dykas, Shaver & Nipper

(57) ABSTRACT

A novel process for the purification of crude aromatic carboxylic acids, such as, for example, terephthalic acid, orthophthalic acid, trimesic acid, isophthalic acid, 2,6-naphthalenedicarboxylic acid and pyromellitic acid, which are obtained by oxidising the corresponding aromatic precursors is described; the process is based on the subsequent oxidation in heterogeneous phase of the crude product in aqueous solution.

12 Claims, No Drawings

PROCESS FOR THE PURIFICATION OF AROMATIC CARBOXYLIC ACIDS

The present invention relates to a novel process for the purification of crude aromatic carboxylic acids, such as, for example, terephthalic acid, orthophthalic acid, trimesic acid, isophthalic acid, 2,6-naphthalenedicarboxylic acid and pyromellitic acid, which are obtained by oxidising the corresponding aromatic precursors.

STATE OF THE ART

Processes for the production of aromatic mono- and poly-carboxylic acids are well known in the literature; they are normally carried out in liquid phase, using as substrates aromatic compounds having at least one oxidisable substituent group which is attached directly to the carbon atom of the corresponding aromatic nucleus (where the expression "oxidisable substituent group" is intended to indicate any substituent in which a carbon atom is bonded directly to the aromatic nucleus) and which, as a result of oxidation, is converted into a carboxylic group.

The oxidising agent is generally gaseous molecular oxygen, preferably diluted with an inert gas; for obvious practical reasons, air (optionally enriched with molecular oxygen) is the gaseous mixture most commonly used for the purpose; the reactions are carried out in the presence of a catalytic complex composed of one or more metals, normally in the form of salts soluble in the reaction solvent, generally acetic acid, preferably in the presence of an activator.

The processes in question are described, for example, in GB-1063964, U.S. Pat. No. 5,112,592, EP-475926, WO 98/29378, EP-26507 and EP-641597, which are to be regarded as an integral part of the present description.

However, the aromatic acids obtained in accordance with the above-mentioned processes contain a variable amount of impurities, generally aldehydes, originating from the partial oxidation of the corresponding aromatic precursor; typical impurities are, for example, 4-carboxybenzaldehyde (4-CBA) in the case of the production of terephthalic acid, and 3-carboxybenzaldehyde (3-CBA) in the case of isophthalic acid.

The purification of the aromatic mono- and poly-carboxylic acids is normally carried out by subjecting the crude product in aqueous solution, generally a 20 to 25% by weight solution, to a hydrogenation reaction in heterogeneous phase in the presence of suitable catalysts in order to convert the above-mentioned impurities into derivatives that are easier to separate from the desired end product; the hydrogenation reaction is normally carried out at pressures of approximately from 65 to 75 bar and at temperatures of approximately from 250 to 300° C. Processes of that type are described, for example, in United States patents U.S. Pat. No. 3,522,298; U.S. Pat. No. 3,542,863; U.S. Pat. No. 3,584,039; U.S. Pat. No. 3,591,629; U.S. Pat. No. 3,607,921; U.S. Pat. No. 3,726,915; U.S. Pat. No. 3,799,976; U.S. Pat. No. 4,126,638, U.S. Pat. No. 4,260,817, U.S. Pat. No. 4,467,110, U.S. Pat. No. 4,629,715, U.S. Pat. No. 4,892,972, U.S. Pat. No. 5,362,908 and U.S. Pat. No. 5,616,792.

DESCRIPTION OF THE INVENTION

Although the process by hydrogenation is in practice the only process for the purification of crude aromatic carboxylic acids that is currently used industrially, it nevertheless has disadvantages of not inconsiderable importance; it in fact leads to a substantial loss of starting material because the secondary products which are eliminated as a result of reduction are likewise precursors of the same aromatic mono- and/or poly-carboxylic acids.

In the second place, the reducing catalysts used in the purification process normally have a relatively short life period because they are deactivated by the unavoidable traces of oxidising catalytic metals contained in the crude acid originating from the previous oxidative process.

The object of the present invention is therefore to provide a process for the purification of aromatic mono- and poly-carboxylic acids which is substantially free from the above-mentioned disadvantages.

It has now been found, and this constitutes the subject-matter of the present invention, that crude aromatic mono- and/or poly-carboxylic acids obtained by oxidising the corresponding aromatic precursors can be purified by a subsequent oxidation reaction; or by bringing an aqueous solution containing the crude aromatic acid into contact with gaseous oxygen in the presence of an oxidation catalyst in heterogeneous phase.

Thus, it is possible to convert all the impurities originating from the previous oxidation stage almost quantitatively into the end product, with a consequent increase in the overall yield of the process. In addition, the oxidation catalysts used in the purification stage are not poisoned by any traces of oxidising catalytic metals contained precisely in the crude acid; on the contrary, it has surprisingly been found that the presence of traces of the catalytic metals originating from the previous oxidation reaction perform an activating function in respect of the catalyst subsequently used in the purification stage, thus prolonging the half-life period thereof and increasing the overall efficiency of the process.

Finally, the costs involved in managing the present purification process are distinctly lower than those of the prior art processes which are based on the use of gaseous hydrogen, which is substantially more expensive and dangerous than air and, therefore, is more difficult to manage from the point of view of plant safety. As mentioned above, the purification process which constitutes the subject-matter of the present invention is carried out by subjecting the crude acid obtained by oxidising the corresponding aromatic precursors in homogeneous phase to a subsequent oxidation reaction in heterogeneous phase; the process in question is preferably carried out on crude acids obtained by oxidative processes which are in turn carried out in the absence of bromine or its derivatives.

Thus, the crude acid in question is dissolved in a 5–40% by weight, preferably a 15–25% by weight, aqueous solution which is subsequently brought into contact with gaseous oxygen in the presence of an oxidation catalyst in solid phase. For obvious economic and practical reasons, air, optionally enriched with molecular oxygen, is preferably used as an alternative to pure gaseous oxygen; the air can be fed in either from the bottom or from the top of the reactor.

The purification/oxidation reaction is normally carried out at a temperature of from 150 to 350° C., preferably at from 250 to 300° C.

The operating pressure must also be maintained at a value such as to ensure that the crude acid remains in solution; normally, the purification/oxidation reaction will be carried out at a pressure of from 20 to 150 bar, preferably at a pressure of from 50 to 100 bar.

The above-mentioned reaction is also normally carried out with residence times of from 1 minute to a few hours, preferably from 1 to 30 minutes; the expression "residence time" means the ratio of the volume of the catalytic bed to the volumetric flow of the crude solution.

As regards the oxidation catalyst, the choice thereof is neither binding nor limiting; for the purposes of the present invention it is in fact possible to use the various supported oxidative catalytic systems currently on the market. The catalytic metal is nevertheless normally selected from those belonging to groups VIII, VIIB and IVB according to the notation adopted in Perry, *Chemical Engineers' Handbook,* 6th Edition, and cerium; the preferred metals for implementing the invention are platinum, palladium and/or ruthenium.

The catalytic metal is normally supported on an inert material under the pressure and temperature conditions of the purification/oxidation reaction, that is to say, in order to prevent the formation of further impurities; the inert material is preferably selected from alumina, titanium dioxide, silicon carbide, activated carbon, or a mixture of cerium and zirconium oxides.

The catalytic metal is normally supported on the inert material in an amount of from 0.3 to 5% by weight, preferably in an amount of from 1.5 to 2.5% by weight, and even more preferably 2% by weight.

In the most advantageous embodiment of the invention, an aqueous solution containing from 15 to 25% by weight of the crude acid is brought into contact with air in the presence of a metal catalyst (selected from platinum, palladium and ruthenium) supported on alumina, titanium dioxide, silicon carbide or activated carbon, for a residence time of from 1 to 30 minutes, at a temperature of approximately 270° C. and at a pressure of from 70 to 80 bar. The following Examples are for purely illustrative purposes and are therefore not to be regarded as limiting the invention.

EXAMPLE 1

A 20% suspension of crude terephthalic acid in water (2100 ppm of 4-carboxybenzaldehyde) is brought to a temperature of 270° C. and to a pressure of approximately 70 bar in order to solubilise the acid completely and to obtain a homogeneous solution. The solution so obtained is fed into a reactor containing a bed of activated carbon granules charged with 0.5% of Engelhard 4911 metallic palladium. The pressure in the reactor is maintained at approximately 80 bar by feeding air into the reactor; the residence time of the solution is 30 minutes. On leaving the reactor, the solution is sent for crystallisation. The terephthalic acid so obtained contains: 4-CBA=<20 ppm and paratoluic acid <150 ppm.

EXAMPLE 2

As Example no. 1, using a catalyst obtained by charging approximately 2% of Engelhard Q318-01 ruthenium onto a Rhodia CR3 support (approximately 9% of zirconium oxide+approximately 91% of cerium oxide); the residence time of the solution is 15 minutes.

After crystallisation, the terephthalic acid has a content of 4-CBA <15 ppm.

EXAMPLE 3

As Example no. 1, using an Engelhard catalyst containing 2% of metallic palladium on a titanium dioxide support; the residence time of the solution is 15 minutes.

The content of 4-CBA is <15 ppm.

What is claimed is:

1. A process for the purification of crude aromatic mono- and/or poly-carboxylic acids obtained by oxidising the corresponding aromatic precursors, characterised in that an aqueous solution containing the crude aromatic acid is brought into contact with gaseous oxygen in the presence of an oxidation catalyst in heterogeneous phase.

2. A process according to claim 1, characterised in that the aqueous solution contains from 5 to 40% by weight of the crude aromatic acid.

3. A process according to claim 2, characterised in that the aqueous solution contains from 15 to 25% by weight of the crude aromatic acid.

4. A process according to claim 1, characterised in that it is carried out at a temperature of from 150 to 350° C.

5. A process according to claim 4, characterised in that it is carried out at a temperature of from 250 to 300° C.

6. A process according to claim 1, characterised in that it is carried out at a pressure of from 20 to 150 bar, preferably from 50 to 100 bar.

7. A process according to claim 1, characterised in that the oxidation catalyst is a metal selected from those belonging to groups VIII, VIIB and IVB and cerium.

8. A process according to claim 7, characterised in that the metal is selected from platinum, palladium and ruthenium.

9. A process according to claim 7, characterised in that the metal is supported on an inert material under the pressure and temperature conditions of the oxidation reaction.

10. A process according to claim 7, characterised in that the metal is supported on the inert material in an amount of from 1 to 5% by weight relative to the inert material.

11. A process according to claim 10, characterised in that the metal is supported on the inert material in an amount of from 1.5 to 2.5% by weight, preferably 2% by weight.

12. A process according to claim 7, characterised in that the inert material is selected from alumina, titanium dioxide, silicon carbide, activated carbon, or a mixture of cerium and zirconium oxides.

* * * * *